(12) United States Patent
Tornøe (10) Patent No.: US 6,555,674 B2
(45) Date of Patent: Apr. 29, 2003

(54) JET PROMOTER

(75) Inventor: Jens Tornøe, Ballerup (DK)

(73) Assignee: NsGene A/S, Ballerup (DK)

( * ) Notice: Subject to any disclaimer, the term of this patent is extended or adjusted under 35 U.S.C. 154(b) by 0 days.

(21) Appl. No.: 09/924,346

(22) Filed: Aug. 8, 2001

(65) Prior Publication Data

US 2002/0098547 A1 Jul. 25, 2002

Related U.S. Application Data (60) Provisional application No. 60/224,087, filed on Aug. 9, 2000.

(51) Int. Cl.$^7$ .............................. C07H 21/04; C12N 5/10
(52) U.S. Cl. .................... 536/24.1; 435/320.1; 435/325; 435/353
(58) Field of Search ...................... 536/24.1; 435/320.1, 435/325, 353

(56) References Cited

FOREIGN PATENT DOCUMENTS

| WO | WO 98/07846 A1 | 2/1998 |
|----|----------------|--------|
| WO | WO 98/32869 A1 | 7/1998 |

OTHER PUBLICATIONS

Alignment of SEQ ID No. 1 as claimed in claim 10 v. Accession No. AAV45337 from Johansen (WO 98/32869).*
Zilberman et al. (1998). *Circulation Research* "Evolutionarily Conserved Promoter Region Containing CarG*–Like Elements Is Crucial for Smooth Muscle Myosin Heavy Chain Gene Expression" 82: 566–575.

Madsen et al. (1997). *J. Biol. Chem.* "Expression of the Smooth Muscle Myosin Heavy Chain Gene Is Regulated by a Negative–acting GC–rich Element Located Between Two Positive–acting Serum Response Factor–binding Elements*" 272: 6332–6340.

Nettlebeck et al. (2000). *Trends in Genetics* "Gene Therapy Designer Promoters for Tumour Targeting" 16: 174–181.

Renfranz et al. (1991). *Cell* "Region–Specific Differentiation of the Hippocampal Stem Cell Line HiB5 upon Implantation into the Developing Mammalian Brian" 66: 713–729.

Maniatis et al. (1987). *Science* "Regulation of Inducible and Tissue–Specific Gene Expression" 236: 1237–1245.

Tornøe, Jens "Synthetic Promoters for CNS Gene Therapy" Department of Molecular Biology, NSGene A/S, section of Microbiology, Biocentrum, Technical University of Denmark. Ph.D. Thesis Jan. 2002.

* cited by examiner

*Primary Examiner*—James Ketter
*Assistant Examiner*—Bronwen M. Loeb
(74) *Attorney, Agent, or Firm*—Mintz Levin Cohn Ferris Glovsky & Popeo PC; Ivor R. Elrifi; Scott D. Miller

(57) ABSTRACT

The JeT promoter is a recombinant promoter with transcriptional activity comparable to a number of strong mammalian promoters. The promoter consists of five key elements: (1) a TATA box; (2) a transcription initiation site (Inr); (3) a CAT consensus sequence in conjunction with (4) a CArG element and finally, (5) four Sp1 transcription binding sites (GGGCGG) arranged in two tandems.

9 Claims, 2 Drawing Sheets

FIG. 1

```
         EcoRI   Sp1            Sp1              CAT
  1   GAATTCGGGCGGAGTTAGGGCGGAGCCAATCAGCCGTGCGCCCGTTCCGAAA
                    CArG            Sp1              Sp1           TATA
 51   GTTGCCTTTTTATGGCTGGGCGGAGAATGGGCGGTGAACGCCGATGATTAT
         box                                Initiation site(Inr)
101   ATAAGGAACGCGCCCGGGTGTGGCACAGCTAGTTCCGTCGCAGCCGGGATTT
                                                BamHI
151   GGGTCGCGGGTTCTTGTTTGTGGATCCCTGTGATCGTCACTTGACA
```

JET PROMOTER

RELATED APPLICATION

This application claims priority to U.S. Ser. No. 60/224,087, filed Aug. 9, 2000 which is incorporated herein by reference in its entirety.

FIELD OF THE INVENTION

This invention concerns the expression of polynucleotides and, in particular, the JeT promoter.

BACKGROUND OF THE INVENTION

Metabolic engineering of living organisms is still in its infancy with respect to industrial applications, despite the fact that genetic engineering is now feasible. To a large extent, this may be due to the disappointing outcome of many of the attempts so far to improve strain performance. There are at least two reasons for the negative outcome of the attempts to increase metabolic fluxes:

One is that the genetic engineer tends to overlook the subtlety of control and regulation of cellular metabolism. For example, a branching flux in a pathway can be eliminated by deleting a gene. Quite often, this will have secondary effects on the metabolism, for instance by lowering metabolite concentrations that are essential to other parts of the cellular metabolism (e.g. processes that are essential to the growth of the organism) and the net result may be that the overall performance of the cell with respect to the desired product is decreased. Instead, it is necessary to tune the expression of the relevant gene around the normal expression level and determine the optimal expression level, for instance as the level that maximizes or minimizes the flux.

The second reason for the negative outcome lies in the rate-limiting concept itself: both metabolic control theory (Kacser & Burns, 27 Symp. Soc. Exp. Biol. 65104 (1973)) and experimental determinations of control by individual steps in a pathway (Schaaff et al., 5 Yeast 285–290 (1989); Jensen et al., 12. EMBO J. 1277–1282 (1993)) have shown that reaction steps which were expected to be rate limiting with respect to a particular flux, turned out to have no or very little control over the flux. Instead, the control and regulation of the cellular metabolism turned out to be distributed over several enzymes in a pathway, and it may be necessary to enhance the expression of several enzymes in order to obtain a higher flux. According to metabolic control theory, the total flux control exerted by all the enzymes in a pathway, should always sum up to 1. Therefore, after one enzyme concentration has been optimized, the flux control will have shifted to another enzyme, and it may then be useful to perform additional rounds of enzyme optimization in order to increase the flux further.

In summary, flux optimization requires (1) fine-tuning of enzyme concentration rather than many fold over expression and often (2) optimization of the level of several enzymes in a pathway rather than looking for the rate limiting step. As a result, there is a need for promoters that can be useful for addressing flux optimization.

SUMMARY OF THE INVENTION

Figure 1:
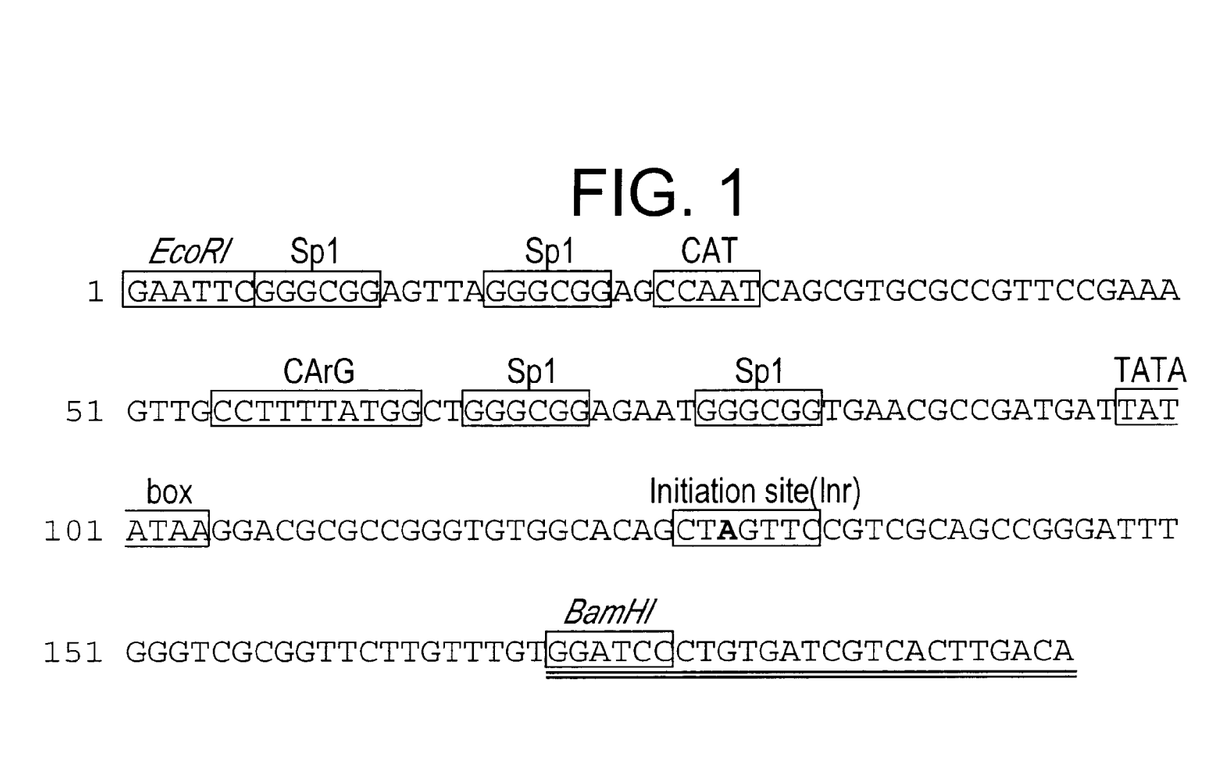
FIG. 1 (SEQ ID NO:1) shows the sequence of the Jet promoter.

The JeT promoter (SEQ. ID. NO:1) takes advantage of a unique combination of transcription factor binding sites resulting in transcriptional activity comparable to a number of strong mammalian promoters such as the simian virus 40 (SV40) and ubiquitin (UbC) promoters. The promoter consists of five key elements:

(1) a TATA box (TATATAA) (SEQ. ID. NO:2),
(2) a transcription initiation site (Inr) (CTAGTTC) (SEQ. ID. NO:3),
(3) a CAT consensus sequence (CCAAT) (SEQ. ID. NO:4) in conjunction with
(4) a CArG element (CCTTTTATGG) (SEQ. ID. NO:5) and finally,
(5) four Sp1 transcription binding sites (GGGCGG) (SEQ. ID. NO:6) arranged in two tandems. The CAT/CArG complex is also referred to as a Serum Response Element (SRE). The JeT promoter sequence is depicted in FIG. 1 with the consensus boxes marked.

DETAILED DESCRIPTION OF THE INVENTION

An important part of selecting a set of consensus sequences that can direct strong expression from a synthetic promoter is choosing the length of the sequences intervening the consensus sites. To mediate a positive effect on promoter activity, transcription factors must not only bind to the promoter sequence, the transcription factors must also be able to interact with each other optimally in order to enhance transcription from the promoter. In several cases it has been shown that even small changes in the intervening sequence between two cooperatively functioning transcription factor binding sites can drastically alter promoter activity (see, PCT International patent application WO 98/07846, incorporated herein by reference). For this reason, the length of the DNA regions separating the chosen consensus boxes have been carefully chosen to mimic wild type promoters.

The activity of the JeT promoter has been compared to different derivatives of the ubiquitin (UbC) promoter using d4EGFP reporter assays (measuring the fluorescence from the expressed Green Fluorescent Protein) in rat hippocampal HiB5 cells. Here, the JeT promoter drives strong and sustained expression of d4EGFP to significant higher levels than the ubiquitin promoter.

Promoter construction. The promoter was constructed from two oligonucleotides, oJeT (SEQ. ID. NO:7) and oLinker (SEQ. ID. NO:8):

```
oJeT:
5'-ATCGAATTCGGGCGGAGTTAGGGCGGAGGCCAATCAGCGTGCGCCGTTCC   (SEQ. ID. NO:7)

GAAAGTTGCCTTTTATGGCTGGGCGGAGAATGGGCGGTGAACGCCGATGATT

ATATAAGGACGCGCCGGGTGTGGCACAGCTAGTTCCGTCGCAGCCGGG-3'
``` oLinker:
5'-CAG<u>GGATCC</u>ACAAACAAGAACCGCGACCCAA (SEQ. ID. NO:8).

AT<u>CCCGGCTGCGACGGAACTAGCTG</u>-3'

Bases underlined with a single line mark the overlapping region of the two oligonucleotides. Restriction endonuclease recognition sites are indicated in FIG. 1 (EcoRI site in 0JeT1 BamHI site in oLinker). Double stranded DNA was made from the oligonucleotides by polymerization in a thermocycler: a 100 µl reaction mix consisting of 2 µM oJeT, 2 µM oLinker, 200 µM dNTP, 2.5 µM MgCl$_2$, 1×Taq DNA polymerase buffer (Amersham Pharmacia Biotech, Uppsala, Sweden) was subjected to heating to 96° for 5 minutes, 5 units Taq polymerase (Amersham Pharmacia Biotech, Uppsala, Sweden) was added followed by annealing and elongation for 10 minutes at 55° C. The polymerization product was run on a 2% agarose gel. Double stranded DNA of the expected size (182 base pairs) was purified from the gel using the QIAquick Gel Extraction Kit (QIAGEN, Hilden, Germany).

The term JeT "functional fragment" refers to a polynucleotide having a sequence that is shorter than the sequence provided in SEQ. ID. NO:1, but which retains JeT promoter activity, i.e., enhanced promoter activity as compared to ubiquitin promoters (see, FIG. 2).

Cloning in reporter vector. The polymerized product was cloned in a reporter vector containing an unstable variant of Enhanced Green Fluorescent Protein, D4EGFP (CLONTECH), using the EcoRI and BamH1 restriction sites. The vector obtained was named pJeTd4E. The part of the JeT promoter including the BamH1 restriction site and downstream bases (doubly underlined in FIG. 1) had been fused directly to the start codon of d4EGFP by PCR. The JeT promoter sequence was verified by sequencing in pJeTd4E.

Figure 2:
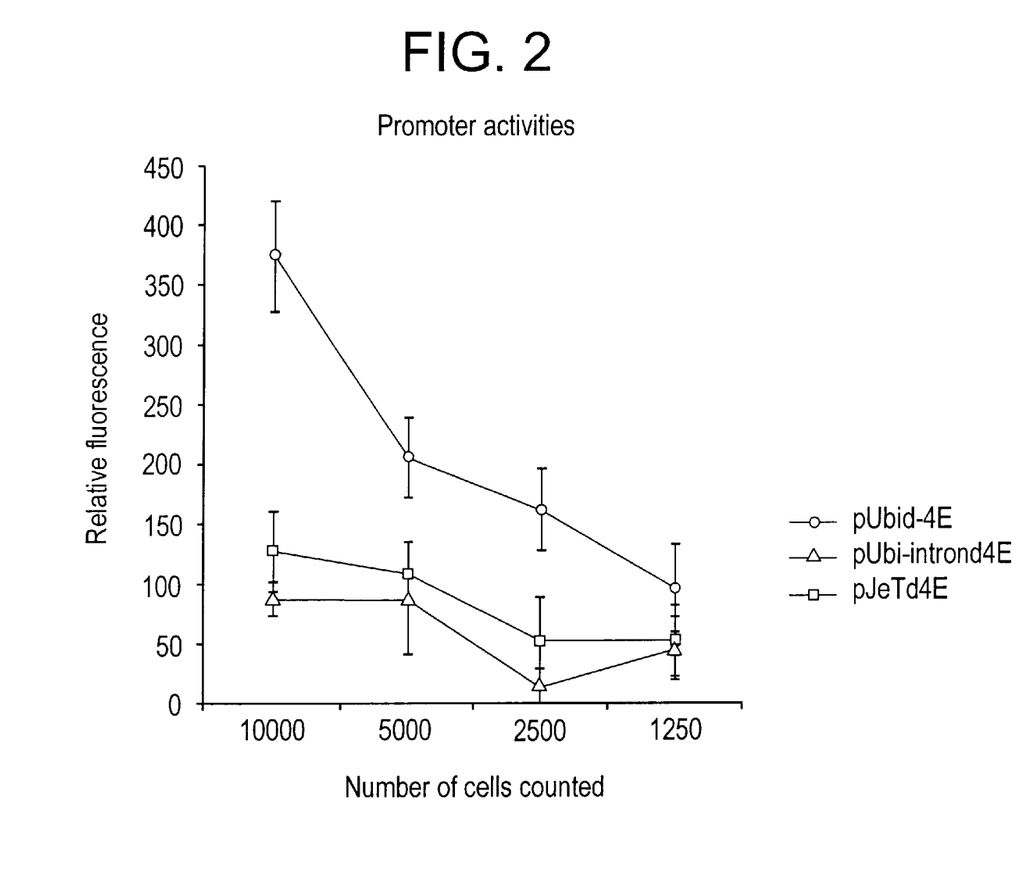
FIG. 2 shows the promoter activity of the JeT promoter as compared with ubiquitin promoters.

Assay of promoter activity. pJeTd4E was transiently transfected in rat hippocampal HiB5 cells using Lipofectamine (GIBCO, Life Technologies A/S, Tåstrup, Denmark). Forty-eight hr after transfection, d4EGFP activity of a fixed number of cells was assayed using a fluor-scanner (FIG. 2).

Use of the invention. Typically, a promoter is operably linked to an enhancer region. An "enhancer" is a region of a polynucleotide (usually cis, or on the same polynucleotide as, a promoter) to which factors bind, thus modulating gene expression from the promoter. As used herein, the term "modulate" means that an promoter is controlled or regulated, resulting in the "down-regulation" or "up-regulation" of the element, depending on the desired effect. By "operably linked" is meant that the coding polypeptide and the promoter are functionally connected to permit gene expression when the appropriate factors are bound to the enhancer, promoter, and other regulatory regions of the polynucleotide. An enhancer operably linked to a promoter is located so that expression of a coding polypeptide can be achieved under conditions compatible with the enhancer function. The orientation or placement of the elements of the vector is not strict, so long as the operable linkage requirement is fulfilled for control of and expression of the coding polynucleotide.

Included in the invention is an isolated DNA that includes a JeT promoter. The term "isolated" refers to molecules separated from other DNA or RNA molecules that are present in the natural source of the regulatory sequence. The term also refers to a nucleic acid or peptide that is substantially free of cellular material, viral material, or culture medium when produced by recombinant DNA techniques, or chemical precursors or other chemicals when chemically synthesized. An isolated nucleic acid includes nucleic acid fragments that are not naturally occurring as fragments and would not be found in the natural state. The term "isolated" is also used herein to refer to polypeptides which are isolated from other cellular proteins and is meant to encompass both purified and recombinant polypeptides.

The term "silencer", also referred to herein as "silencer element" is intended to include regulatory elements capable of decreasing, inhibiting, or repressing transcription from a basic promoter.

A "coding polynucleotide" is a polynucleotide that can be transcribed into mRNA, which is then translated into a polypeptide. The boundaries of the coding polypeptide are determined by a translation start codon at the 5'-terminus and a translation stop codon at the 3'-terminus. A coding sequence can include, but is not limited to mRNA, cDNA, and recombinant polynucleotide sequences. An "open reading frame" (ORF) is a region of a coding polynucleotide that encodes a polypeptide; this open reading frame may represent a portion of a coding sequence or a total coding sequence. When a promoter is operably linked to a coding polynucleotide, the promoter can effect the expression of the coding polynucleotide.

The coding polynucleotide can be a "transgene" is a polynucleotide inserted by artifice into a cell, so that the polynucleotide becomes part of the genome of an organism (i.e., either stably integrated or as a stable extrachromosomal element) that develops from that cell. The term "transgenic" includes any recombinant genetic technology familiar to those in the art used to produce an organism carrying a transgene. Such a transgene may include a gene which is partly or entirely heterologous (i.e., foreign) to the transgenic organism, or may represent a gene homologous to an endogenous gene of the organism. The transgene can be a reporter gene. A "reporter gene" is a gene whose expression may be assayed. Such genes include, without limitation, thymidine kinase (tk), neomycin transferase (neo), β-galactosidase (lacZ), -glucuronidase (GUS), amino acid biosynthetic genes (e.g. the yeast LEU2 gene), the mammalian chloramphenicol transacetylase (CAT) gene, an alkaline phosphatase gene, a luciferase gene (e.g., the luciferase gene present in pGL3-basic (Promega Corp., Madison, Wis.)), or green fluorescent protein genes (see, FIG. 2).

In principle, the JeT promoter according to the invention can be constructed for use in any living organism, preferably for modulating gene expression of eukaryotic microorganisms and cell lines. In connection with this invention the term "microorganism" broadly includes prokaryotic organisms such as bacteria as well as eukaryotic microorganisms such as yeasts, other fungi and cell lines of higher organisms and, in particular, rat hippocampal HiB5 cells.

This invention is preferably used with organisms selected from the group consisting of eukaryotic microorganisms such as yeasts, other fungi and mammalian cell lines. An interesting eukaryotic microorganism is the yeast species *Saccharomyces cerevisiae*, normal baker's yeast. In promoters to be used in Saccharomyces the consensus sequences may further comprise a transcription initiation signal (TI box) functioning in *Saccharomyces cerevisiae*.

The regulation of transcription initiation in the eukaryotic cell is complex compared to the prokaryote. The transcription start site is normally preceded by a so called TATA box that contains the consensus sequence TATAAA or parts hereof, but unlike in the prokaryote, the distance from the TATA box to the transcription start site is much less defined. In *Saccharomyces cerevisiae* this distance is typically 40–120 nucleotides (Oliver & Warmington, in 3 *The Yeasts*, Rose & Harrison, eds., 117–160 (Academic Press, London, 1989)). The so-called −35 consensus hexamer which is found in many prokaryotic promoters is absent in *Saccharomyces cerevisiae*. Instead so-called upstream activation sequences (UAS) are found upstream of the transcription initiation site. These UAS are recognised by specific DNA binding proteins that can then act as activators of transcription initiation. For instance, the UAS sequence that is found upstream of the genes involved in amino acid biosynthesis, UASGCN4p, consists of a DNA sequence that specifies a binding site for the GCN4 protein, which activates the transcription of these genes (Hinnebusch, in *The Molecular and Cellular Biology of the Yeast Saccharomyces*, Jones et al., eds. 319–414 (Gene Expression. Cold Spring Harbor Laboratory Press, Cold Spring Harbor, N.Y., 1992)). The distance between the TATA box and the UAS sequence in eukaryotic promoters is highly variable and may be up to about 1000 bp (see, PCT International patent application WO 98/07846, incorporated herein by reference). Some genes even contain more than one copy of the UAS, but one seems to be sufficient for activation.

Polynucleotides can encode desirable polypeptides, including peptides fused to carrier proteins. Polypeptides can be encoded by either a synthetic or recombinant polynucleotide. The term "recombinant" refers to the molecular biological technology for combining polynucleotides to produce useful biological products, and to the polynucleotides and peptides produced by this technology. The polynucleotide can be a recombinant construct (such as a vector or plasmid) which contains the coding polynucleotide under the operative control of polynucleotides encoding regulatory elements such as promoters, termination signals, and the like, including the JeT promoter. A control sequence operatively linked to a coding sequence is ligated such that expression of the coding sequence is achieved under conditions compatible with the control sequences. "Control sequence" refers to polynucleotide sequences which are necessary to effect the expression of coding and non-coding sequences to which they are ligated. Control sequences generally include promoter, ribosomal binding site, and transcription termination sequence. In addition, "control sequences" refers to sequences which control the processing of the peptide encoded within the coding sequence; these can include, but are not limited to sequences controlling secretion, protease cleavage, and glycosylation of the peptide. The term "control sequences" is intended to include, at a minimum, components whose presence can influence expression, and can also include additional components whose presence is advantageous, for example, leader sequences and fusion partner sequences. A "coding sequence" is a polynucleotide sequence which is transcribed and translated into a polypeptide. Two coding polynucleotides are "operably linked" if the linkage results in a continuously translatable sequence without alteration or interruption of the triplet reading frame. A polynucleotide is operably linked to a gene expression element if the linkage results in the proper function of that gene expression element to result in expression of the coding sequence (such as is shown in FIG. 2, for example). "Transfection" is the insertion of an exogenous polynucleotide (i.e., a "transgene") into a host cell. The exogenous polynucleotide is integrated within the host genome. A polynucleotide is "capable of expressing" a polypeptide if it contains nucleotide sequences which contain transcriptional and translational regulatory information and such sequences are "operably linked" to coding polynucleotides. A polynucleotide that encodes a peptide coding region can be then amplified, for example, by preparation in a bacterial vector, according to conventional methods known to those of skill in the art of molecular biology, for example, described in the standard work Sambrook et al., *Molecular Cloning: A Laboratory Manual* (Cold Spring Harbor Press 1989). Expression vehicles include plasmids or other vectors.

The polynucleotides of the invention, including the JeT promoter and polynucleotides under the control of the JeT promoter can be prepared by chemical synthesis methods or by recombinant techniques. The polypeptides can be prepared conventionally by chemical synthesis techniques, such as described by Merrifield, 85 J. Amer. Chem. Soc. 2149–2154 (1963) (see, Stemmer et al, 164 Gene 49 (1995)). Synthetic genes, the in vitro or in vivo transcription and translation of which will result in the production of the protein can be constructed by techniques well known in the art (see, Brown et al., 68 Methods in Enzymology 109–151 (1979)). The coding polynucleotide can be generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404).

Alternatively, systems for cloning and expressing polynucleotides encoding desirable polypeptides (using the JeT promoter) include various microorganisms and cells which are well known in recombinant technology. These include, for example, various strains of *E. coli, Bacillus, Streptomyces,* and Saccharomyces, as well as mammalian, yeast and insect cells. Suitable vectors are known and available from private and public laboratories and depositories and from commercial vendors. See, Sambrook et al., *Molecular Cloning: A Laboratory Manual* (Cold Spring Harbor Press 1989). See, also PCT International patent application WO 94/01139). These vectors permit infection of patient's cells and expression of the synthetic gene sequence in vivo or expression of it as a peptide or fusion protein in vitro.

Polynucleotide gene expression elements useful for the expression of cDNA encoding peptides include, but are not limited to (a) viral transcription promoters and their enhancer elements, such as the SV40 early promoter, Rous sarcoma virus LTR, and Moloney murine leukemia virus LTR; (b) splice regions and polyadenylation sites such as those derived from the SV40 late region; and (c) polyadenylation sites such as in SV40. Recipient cells capable of expressing the HIV vaccine candidate gene product are then transfected. The transfected recipient cells are cultured under conditions that permit expression of the desirable polypeptide products, which are recovered from the culture. Host mammalian cells, such as Chinese Hamster ovary cells (CHO) or COS-1 cells, can be used. These hosts can be used in connection with poxvirus vectors, such as vaccinia or swinepox. Suitable non-pathogenic viruses which can be engineered to carry the synthetic gene into the cells of the host include poxviruses, such as vaccinia, adenovirus, retroviruses and the like. A number of such non-pathogenic viruses are commonly used for human gene therapy, and as carrier for other vaccine agents, and are known and selectable by one of skill in the art. The selection of other suitable host cells and methods for transformation, culture, amplification, screening and product production and purification can be performed by one of skill in the art by reference to known techniques (see, e.g., Gething &

Sambrook, 293 Nature 620–625 (1981)). Another preferred system includes the baculovirus expression system and vectors.

Determinations of the sequences for the polynucleotide coding region that codes for the desirable polypeptide, for the JeT promoter, or for polynucleotides for related uses described herein can be performed using commercially available computer programs, such as DNA Strider and Wisconsin GCG. Owing to the natural degeneracy of the genetic code, the skilled artisan will recognize that a sizable yet definite number of DNA sequences can be constructed which encode the claimed peptides (see, Watson et al., *Molecular Biology of the Gene*, 436–437 (the Benjamin/Cummings Publishing Co. 1987)).

Recombinant genetic techniques. A recombinant polynucleotide containing a regulatory region of the invention can be constructed in a standard DNA expression vector and introduced to a cell for expression within the cell. The term "recombinant" refers to a product of human intervention. Polynucleotides for insertion into cloning vectors, for example regulatory regions, can be constructed using the polymerase chain reaction (PCR) to amplify appropriate polynucleotides. Polynucleotide synthesis and purification techniques are described in Sambrook et al., *Molecular Cloning: A Laboratory Manual* (Cold Spring Harbor Laboratory Press, 1989); *Current Protocols in Molecular Biology*, Ausubel et al., eds., (Wiley Interscience, N.Y. 1993), and *Molecular Biology LabFax* (Brown, ed., Academic Press, 1991). The PCR procedure is performed by well-known methodology (see, for example, Bangham, in *Protocols in Molecular Genetics* (Humana Press, 1991)). Moreover, PCR kits can be purchased from companies such as Stratagene Cloning Systems (La Jolla, Calif. and Invitrogen (San Diego, Calif.). The products of PCR are subcloned into cloning vectors. The use of PCR for bacterial host cells is described, for example, by Hofmann et al., in *PCR Protocols and Applications* White, ed. (Humana Press, 1993) pp. 205–210), and by Cooper et al., in *PCR Protocols and Applications* White, ed. (Humana Press, 1993) at pp. 305–316). "Host cells" are cells in which a vector can be propagated and the vector DNA can be expressed.

A "vector" is a replicon to which regulatory region is attached, so as to bring about the replication or expression of a coding polynucleotide. Vectors can be used for the transformation of cells in gene manipulation bearing a coding polynucleotide corresponding to appropriate polypeptides that, when combined with appropriate regulatory region, confer specific properties on the transformed cell. Recombinant vectors are constructed by cutting and joining polynucleotides from different sources using restriction enzymes and ligases. Any of many vectors can be employed for this purpose. Factors of importance in selecting a particular vector include the ease with which host cells that contain the vector may be recognized and selected from those host cells which do not contain the vector.

Vectors include cloning vectors and expression vectors. A cloning vector is a polynucleotide, such as a plasmid, cosmid or bacteriophage, that can replicate autonomously in a host prokaryotic or eukaryotic cell. Cloning vectors typically contain one or a small number of restriction endonuclease recognition sites at which polynucleotide sequences can be inserted in a determinable fashion without loss of an essential biological function of the vector, as well as a marker gene that is suitable for use in the identification and selection of cells transformed with the cloning vector. Suitable cloning vectors are described by Sambrook et al., *Molecular Cloning: A Laboratory Manual* (Cold Spring Harbor Laboratory Press, 1989); *Current Protocols in Molecular Biology*, Ausubel et al., eds., (Wiley Interscience, N.Y. 1993), and *Molecular Biology LabFax* (Brown, Ed., Academic Press, 1991). Cloning vectors can be obtained, for example, from GIBCO/BRL (Gaithersburg, Md.), Clontech Laboratories, Inc. (Palo Alto, Calif.), Promega Corporation (Madison, Wis.), Stratagene Cloning Systems (La Jolla, Calif.), Invitrogen (San Diego, Calif.), and the American Type Culture Collection (Rockville, Md.).

Cloned variants are amplified by transforming competent bacterial cells with a cloning vector and growing the bacterial host cells in the presence of the appropriate antibiotic (see, for example, Sambrook et al., and Ausubel et al. PCR is then used to screen bacterial host cells for the appropriate clones).

The resulting recombinant polynucleotide or relevant parts can be cloned from cloning vectors into expression vectors, which expression vectors have characteristics permitting higher levels of, or more efficient expression of, the resident polynucleotides.

Vectors of the invention. The invention further provides vectors containing the regulatory region operably linked to coding polynucleotides. Many genetic constructs and methods for expressing heterologous genes in cells of mammals are known in the art and are suitable for use with the regulatory region of the invention. For example, the construction can be accomplished with conventional methods, such as those that employ viral vectors (e.g., vectors derived from retroviruses, adenoviruses, herpes viruses, vaccinia viruses, polio viruses, sindbis viruses, adeno-associated viruses, and other DNA and RNA viruses.). In addition, the invention is suitable for methods involving direct injection of recombinant polynucleotide of the invention, in which the recombinant polynucleotide is either chemically encapsulated or not (i.e., exists as free DNA; "naked DNA").

Expression vectors. The invention provides recombinant polynucleotides in a recombinant expression vector. The term "expression vector" refers to a plasmid, virus or other vehicle known in the art that has been manipulated by insertion or incorporation of the target genetic sequences. Such expression vectors contain a promoter which facilitates the efficient transcription of the inserted genetic sequence of the host. The expression vector typically contains the regulatory region or the promoter of the invention.

For a mammalian host, several possible vector systems are available for expression of the polynucleotide specific for a targeted transcript. Some vectors use DNA elements which provide autonomously replicating extra-chromosomal plasmids, generally derived from animal viruses. Other vectors include vaccinia virus expression vectors. Still other vectors integrate the desired polynucleotide into the host chromosome. Cells which have stably integrated the introduced DNA into their chromosomes can be selected by also introducing one or more markers (e.g., an exogenous gene) which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription termination signals. Various techniques can be used for introducing these vectors into mammalian cells, such as protoplast fusion, calcium phosphate precipitation, electroporation or other conventional techniques.

Viral vectors. Virus-like vectors are useful as vehicles for the importation and expression of recombinant polynucleotide constructs in cells. Virus-derived vectors can safely deliver exogenous nucleic acid to a recipient cell. Virus-derived vectors that carry a heterologous gene (transgene) to exploit the natural ability of a virus to deliver genomic content to a target cell are useful for gene therapy to correct genetic disease or to deliver therapeutic molecules. Vectors suitable for use in the present invention include baculovirus-derived vectors for expression in insect cells; microbial expression vectors such as recombinant bacteriophage DNA, plasmid DNA or cosmid DNA expression vectors containing the polynucleotide of the invention; recombinant yeast expression vectors; plant cell recombinant virus expression vectors (e.g., cauliflower mosaic virus, CaMV; tobacco mosaic virus, TMV) or transformed with recombinant plasmid expression vectors (e.g., Ti plasmid) containing the polynucleotide coding sequence; or animal cell recombinant virus expression vectors (e.g., retroviruses, adenovirus, vaccinia virus) containing the polynucleotide coding sequence, or transformed animal cell systems engineered for stable expression.

To produce recombinant viral vectors for mammalian cells, several viruses have been developed. Interest has centered on four types; retroviruses (including lentiviruses), adenoviruses, adeno-associated viruses and herpes simplex virus type 1 (see, David Peel, *Virus Vectors & Gene Therapy: Problems, Promises & Prospects* (MBChB Special Study Module Project Report, Department of Microbiology & Immunology, University of Leicester, 1998)).

Generally, such vectors do not replicate in vivo, precluding any unintended infection of non-target cells. In such cases, helper cell lines are provided which supply the missing replicative functions in vitro, thereby permitting amplification and packaging of the vector encoding the polynucleotide. A further precaution against accidental infection of non-target cells involves the use of target cell-specific regulatory sequences. When under the control of such sequences, polynucleotide constructs would not be expressed in normal tissues (see, U.S. Pat. No. 5,824,544, which provides adenovirus vectors for use in gene therapy that prevent the generation of replication-competent adenovirus during in vitro propagation and clinical use).

Retroviral vectors. Retroviruses are a class of enveloped viruses containing a single stranded RNA molecule as the genome. Following infection, the retroviral genome is reverse transcribed into double stranded DNA, which integrates into the host genome and expresses as proteins. The viral genome contains at least three genes: gag (coding for core proteins), pol (coding for reverse transcriptase) and env (coding for the viral envelope protein). At each end of the genome are long terminal repeats (LTRs) which include regulatory regions and sequences involved with reverse transcription and integration. In addition there are sequences required for packaging the viral DNA (psi) and RNA splice sites in the env gene. In addition to using retroviruses as recombinant vectors for the transfection of polynucleotides to a cell, retroviruses can be used to transform cells by integrating near to a cellular proto-oncogene and driving inappropriate expression from the LTR. This event is termed insertional mutagenesis. Retroviral vectors are frequently used for or gene therapy, because of their ability to integrate into the cellular genome (Jolly, 1 Cancer Gene Therapy 51–64 (1994); Hodgson, 13 BioTechnology 222–225 (1995)).

Retroviral vectors can be based upon the Moloney murine leukemia virus (Mo-MLV). Mo-MLV is an amphotrophic virus, capable of infecting both mouse and human cells. This capability enables vector development in both mouse models and human cells, thus enabling human treatment. The viral genes are replaced with the transgene of interest and expressed on plasmids in the packaging cell line. Because the plasmids lacking non-essential genes lack the packaging sequence (psi) they are not included in the virion particle. (That is, the plasmids containing the structural genes (gag, pol and env) lack the packaging signal. The structural viral genes are essential, at least for virus formation.) To prevent recombination resulting in replication competent retroviruses, all regions of homology with the vector backbone are usually removed and the non-essential genes expressed by at least two transcriptional units (see, Ory et al., 93(21) Proc. Natl. Acad. Sci. USA 11400–06 (1998), who have generated a human 293-derived retroviral packaging cell line (293GPG)).

The essential regions include the 5' and 3' LTRs and the packaging sequence lying downstream of the 5' LTR. Transgene expression can either be driven by the regulatory region in the 5' LTR, or by the regulatory region of the invention. The exact positioning of the transgene start codon and small alterations of the 5' LTR influence transgene expression. To aid identification of transformed cells selectable markers, such as neomycin and β-galactosidase, can be included and transgenes expression can be improved with the addition of internal ribosome sites.

Lentiviruses are a subclass of retroviruses which are able to infect both proliferating and non-proliferating cells. They are considerably more complicated than simple retroviruses, containing an additional six proteins, tat, rev, vpr, vpu, nef and vif. Current packaging cell lines have separate plasmids for a pseudotype env gene, a transgene construct, and a packaging construct supplying the structural and regulatory genes in trans.

The retroviral envelope interacts with a specific cellular protein to determine the target cell range. Altering the env gene or or Env protein can manipulate the cell range, for example by direct modifications of the binding site between the envelope protein and the cellular receptor; replacing a portion of the env gene with 150 codons from the erythropoietin protein (EPO) (see, Kasahara et al., 266 Science 1374–1376 (1994); coupling an antibody to the viral particle with affinity for a second cell specific antibody via a streptovadin bridge (see, Roux et al., 86 Proc. Nat'l Acad. Sci. USA 9079–9083 (1989); and treating viral particles with lactose for uptake by cells, principally hepatocytes, expressing asiaglycoprotein receptors. Because viruses differ with respect to their tropisms, replacing the env gene with that of another virus extends the host range in a technique known as pseudotyping.

Adenovirus vectors. Adenoviruses are non-enveloped viruses containing a linear double stranded DNA genome, which has been well-characterized through studies in classical genetics and molecular biology (Horwitz, in *Virology*, 2nd ed., Fields et al., eds. (Raven Press, New York, 1990). Subgroup C serotypes 2 or 5 are usually used as vectors. The life cycle does not normally involve integration into the host genome, rather adenoviruses replicate as episomal elements in the nucleus of the host cell.

Adenovirus-based vectors offer several unique advantages, including tropism for both dividing and non-dividing cells, minimal pathogenic potential, ability to replicate to high titer for preparation of vector stocks, and the potential to carry large inserts (Berkner, 158 Curr. Top. Micro. Immunol. 39–66 (1992); Jolly, 1 Cancer Gene Therapy 51–64 (1994). The cloning capacity of an adenovirus vector results from the deletion of certain regions of the virus genome dispensable for virus growth (Graham, *J. Gen. Virol.* 36:59–72 (1977)). Adenoviruses have four early transcriptional units (E1, E2, E3 and E4), which have regulatory functions, and a late transcript, which codes for structural proteins. Progenitor vectors have either the E1 or E3 gene inactivated, with the missing gene being supplied in trans either by a helper virus, plasmid or integrated into a helper cell genome (human fetal kidney cells, 293, Graham et al., 36 *J. Gen. Virol.* 59–72 (1977)). Second generation vectors additionally use an E2a temperature sensitive mutant (see, Engelhardt et al., *Human Gene Therapy* 5: 1217–1229 (1994)) or an E4 deletion (see, Armentano et al., *J. Virol.* 71: 2408–2416 (1997)). The "gutless" vectors contain only the inverted terminal repeats (ITRs) and a packaging sequence around the transgene, all the necessary viral genes being provided in trans by a helper virus (Chen et al., 94 Proc. Nat'l Acad. Sci. USA 1645–1650 (1997)).

Adenoviral vectors are very efficient at transfecting cells in vitro and in vivo, and can be produced at high titers. Transgene expression in vivo from progenitor vectors tends to be transient. The development of vectors containing fewer genes, culminating in the "gutless" vectors which contain no viral coding sequences, has resulted in prolonged in vivo transgene expression in liver tissue (Schieder et al., 18 Nature Genetics 180–183 (1998)).

Uptake of the adenovirus particle is a two stage process involving an initial interaction of a fiber coat protein in the adenovirus with a cellular receptor or receptors, then binding to the integrin family of cell surface heterodimers, allowing internalization via receptor mediated endocytosis. Methods of increasing viral uptake include stimulating the target cells to express an appropriate integrin (see, Davison et al., 71 J. Virol. 6204–6207 (1997)) and conjugating an antibody with specificity for the target cell type to the adenovirus (see, Goldman et al., 57 Cancer Res. 1447–1451 (1997)).

Adeno-associated viruses. Adeno-associated viruses (AAV) are non-pathogenic human parvoviruses, dependent on a helper virus to proliferate. AAV are capable of infecting both dividing and non dividing cells, and in the absence of a helper virus integrate into a specific point of the host genome (chromosome 19q 13-qter) at a high frequency. The wild type genome is a single stranded DNA molecule, consisting of two genes; rep, coding for proteins which control viral replication, structural gene expression and integration into the host genome, and cap, which codes for capsid structural proteins. At either end of the genome is a terminal repeat (TR), containing an AAV promoter: Viral vectors that are derived from AAV offer many potential advantages.

Recombinant AAV can also efficiently integrate into the host genome, can transduce non-dividing cells, and does not induce an immune response which destroys the transfected cells. When used as a vector, the rep and cap genes are replaced by the transgene and its associated regulatory sequences. Production of the recombinant vector requires that rep and cap are provided in trans, along with helper virus gene products The conventional method is to co-transfect two plasmids, one for the vector and another for rep and cap, into cells infected with adenovirus. More recent protocols remove all adenoviral structural genes and use rep resistant plasmids (see, Xiao et al., 72 Journal of Virology 2224–2232 (1998)) or conjugate a rep expression plasmid to the mature virus prior to infection (see, Fisher et al., 7 *Human Gene Therapy* 2079–2087 (1996)).

Interest in AAV vectors has been due to AAV integration into the host genome allowing prolonged transgene expression. Gene transfer into hepatic cells has been reported by Snyder et al., 16 Nature Genetics 270–275 (1997).

Herpes simplex virus. Herpes simplex virus type 1 (HSV-1) is a human neurotropic virus. Consequently interest has largely focused on using HSV-1 as a vector for gene transfer to the nervous system. The wild type HSV-1 virus is able to infect neurons and either proceed into a lytic life cycle or persist as an intranuclear episome in a latent state. Latently infected neurons function normally and are not rejected by the immune system.

The HSV-1 viral genome is a linear double stranded DNA molecule. There are two unique regions, long and short (termed UL and US) which are linked in either orientation by internal repeat sequences (IRL and IRS). At the non-linker end of the unique regions are terminal repeats (TRL and TRS). About half of the viral genes are not essential for growth in cell culture. Once these non essential genes have been deleted, foreign DNA can be accommodated within the virus. Three main classes of HSV-1 genes have been identified, namely the immediate-early (IE or α) genes, early (E or β) genes and late (L or gamma) genes.

Two basic approaches have been used for production of HSV-1 vectors, namely amplicons and recombinant HSV-1 viruses. Amplicons are bacterially produced plasmids containing col E1 ori (an *Escherichia coli* origin of replication), OriS (the HSV-1 origin of replication), HSV-1 packaging sequence, the transgene under control of an immediate-early promoter and a selectable. The amplicon is transfected into a cell line containing a helper virus (a temperature sensitive mutant) which provides all the missing structural and regulatory genes in trans. Both the helper and amplicon containing viral particles are delivered to the recipient. More recent amplicons include an Epstein-Barr virus derived sequence for plasmid episomal maintenance (Wang & Vos, 70 J. Virol. 8422–8430(1996)).

Recombinant viruses are made replication deficient by deletion of one the immediate-early genes e.g. ICP4, which is provided in trans. Deletion of a number of immediate-early genes substantially reduces cytotoxicity and also allows expression from promoters that would be silenced in the wild type latent virus, making these promoters of use in directing long term gene expression.

Replication-conditional mutants are only able to replicate in certain cell lines. These mutants are particularly useful for the treatment of cancers, killing the neoplastic cells which proliferate faster than other cell types. Permissive cell lines are all proliferating and supply a cellular enzyme to complement for a viral deficiency.

Non-viral polynucleotides. Non-viral polynucleotide constructs are also useful as vehicles for the importation and expression of recombinant polynucleotide constructs in cells. The recombinant polynucleotides of the invention can be directly injected into tissue. Methods of direct injection of polynucleotides into tissue are described by Blau & Springer, 333(23) N Engl J Med 1554–6 (1995). See also, Blau & Khavari, 3(6) Nat Med 612–3 (1997)

The recombinant polynucleotides of the invention can be chemically encapsulated for transfection, as described by Wu et al., 264(29) J Biol Chem 16985–7 (1989). Wu et al. showed that a foreign gene driven by natural mammalian regulatory elements can be targeted to hepatocytes and the resultant gene expression made to persist. A soluble DNA carrier system was constructed of two covalently linked components: (1) a polycation, poly-L-lysine, that can bind DNA in a strong but non-damaging interaction, and (2) an asialoglycoprotein which can be targeted specifically to hepatocytes by cell surface asialoglycoprotein receptors unique to this cell type. Wu et al. used a plasmid containing mouse albumin regulatory sequences (making this system attractive for use with the recombinant polynucleotide of the invention) and complexed to the carrier system for intravenous injection. By this system, the precombinant polynucleotide of the invention can be delivered to hepatocytes by intravenous injection in vivo using a soluble DNA carrier system. Gene expression targeted in this manner can be made to persist by stimulation of hepatocyte replication.

The recombinant polynucleotide of the invention can also be introduced into cells by the method of Kaneda et al., 243 Science 375–8 (1989). By this method, recombinant polynucleotide of the invention, and nuclear proteins are efficiently transferred into cells. The recombinant polynucleotide is rapidly transported into the nuclei of cultured cells. Moreover, when the recombinant polynucleotide and nuclear protein are cointroduced into nondividing cells in rat liver by injection into rat portal veins, the recombinant polynucleotide is carried into liver cell nuclei efficiently by nuclear protein for expression in the rat liver.

Alternatively, the recombinant polynucleotide of the invention can be introduced into cells by the method of Remy et al., 92(5) Proc Natl Acad Sci USA 1744–8 (1995), a modular transfection system based on lipid-coated polynucleotide particles reminiscent of enveloped viruses. The particle core is composed of the lipopolyamine-condensed polynucleotide in an electrically neutral ratio to which other synthetic lipids with key viral properties are hydrophobically adsorbed. Good transfection level can be achieved simply with the neutral core particle, provided a zwitterionic lipid (dioleoyl phosphatidylethanolamine) is added to completely coat the recombinant polynucleotide. Addition of lipids with a triantennary galactosyl residue drives the neutral nucleolipidic particles to the asialoglycoprotein receptor of liver cells, such as the human hepatoma HepG2 cells: Transfection increases approximately 1000-fold with 25% galactolipid. These electrically silent particles provide an attractive solution for gene transfer in vivo where the external saccharide coat allows the particles to diffuse within the organism and reach target cells.

Cells of the invention. The invention provides transformed cells containing the regulatory region operably linked to coding polynucleotides. A recombinant polynucleotide can be expressed in vitro by DNA transfer into a suitable host cell. "Host cells" are cells in which a vector can be propagated and its DNA expressed. (Note, the replication defective vectors (see above) cannot be propagated in the mammalian cells) The term also includes any progeny of the subject host cell, even those that are not identical to the parental cell due to mutations that occurred during replication. Methods of stable transfer, meaning that the foreign DNA is continuously maintained in the host, are known in the art. When the host cell is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be co-transformed with the polynucleotide of the invention, and a second foreign DNA molecule encoding a selectable phenotype, such as the herpes simplex thymidine kinase gene. Another method is to use a eukaryotic viral vector to transiently or stably infect or transform eukaryotic cells. Host cells may be transformed with the recombinant polynucleotide of the invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan. The techniques of transforming cells with vectors are well known in the art and may be found in such general references as Sambrook et al., *Molecular Cloning: A Laboratory Manual,*(Cold Spring Harbor Laboratory Press, 1989) and *Current Protocols in Molecular Biology,* Ausubel et al., eds. (Wiley Interscience, N.Y. 1993)

Thus, the invention provides transformed cells. A "transformed" cell is a cell or progeny of a cell into which has been introduced, by means of recombinant genetic techniques, a polynucleotide encoding a polypeptide, including a suitable regulatory region. The transformed cell may be any cell that can be easily transfected and can express a polypeptide. Any suitable source of tissue, can be used as a source for generating transformed cells, including publicly available immortalized cell lines and dividing primary cell cultures. Examples of human cell lines include human neural stem or progenitor cells; RPMI 2650, HT-1080 or SW-13 epithelial cells; HL-60 macrophage cells; CCRF-CEM or RPMI 8226 lymphoid cells; and WI-38, HEL1, MRC-5 or IMR-90 fibroblast cells. Other useful cell lines include CV-1, COS, F9, CHO, HeLa, NIH 3T3, HuTu80, Rat2 fibroblast, HT1080.T, chick embryo fibroblast, quail QT6, or Drosophila Schneider S2.

Preferably, the transformed cell contains the factors necessary for optimal gene expression using the enhancer region of the invention, for example, a liver cell, a liver-derived cell, or a cell that can express liver-specific genes, such as an embryonic cell. The transformed cell can be selected from transformed 293, AV12, HepG2, H2.35, or E11B4D cells.

A number of selection systems may be used, including but not limited to the herpes simplex virus thymidine kinase, hypoxanthine-guanine phosphoribosyltransferase, and adenine phosphoribosyl-transferase genes can be employed in tk$^-$, hgprt$^-$ or aprt$^-$ cells respectively. Also, antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to the hygromycin antibiotic. Additional selectable genes have been described, namely trpB, which allows cells to utilize indole in place of tryptophan; hisD, which allows cells to utilize histinol in place of histidine; and ODC (ornithine decarboxylase) which confers resistance to the ornithine decarboxylase inhibitor, 2-(difluoromethyl)-DL-ornithine, DFMO.

Increased expression can be achieved by increasing or amplifying the vector copy number using amplification methods well known in the art. Such amplification methods include, e.g., DHFR amplification (see, e.g., U.S. Pat. No. 4,470,461) or glutamine synthetase ("GS") amplification (see, e.g., U.S. Pat. No. 5,122,464). Expression vectors containing the geneticin (G418) or hygromycin drug selection genes are also useful. These vectors can express both a coding polynucleotide of interest and a gene conferring resistance to selection with toxin such as G418 or hygromycin B. The G418 resistance gene codes for aminoglycoside phosphotransferase (APH) which enzymatically inactivates G418 added to the culture medium. Only those cells expressing the APH gene will survive drug selection usually resulting in the expression of the second biologic gene as well. The hygromycin B phosphotransferase (HBH) gene codes for an enzyme that specifically modifies hygromycin toxin and inactivates it. Genes cotransfected with or contained on the same plasmid as the hygromycin B phosphotransferase gene will be preferentially expressed in the presence of hygromycin B.

Pharmaceutical compositions. The invention provides pharmaceutical compositions containing the regulatory region. The pharmaceutical compositions are the recombinant polynucleotides of the invention in a pharmaceutically acceptable excipient. The invention also provides methods for using the regulatory region for increasing gene expression. The method involves providing a transformed cell containing a recombinant polynucleotide, a regulatory region of the invention operably linked to a coding polynucleotide, and expressing the coding polynucleotide in the cell.

The invention provides methods for using the recombinant polynucleotide of the invention. For example, the invention provides a method for introducing recombinant polypeptide into a cell. The cell is contacted with a recombinant polynucleotide of the invention under conditions that permit the recombinant polypeptide to enter the cell. The contacting can occur in vitro or in vivo. In one embodiment, the contacting involves perfusing tissue with a liquid containing the recombinant polynucleotide. In another embodiment, the contacting is by a route of administration that is intravenous, intramuscular, intradermal, subcutaneous, oral, or topical.

The recombinant polynucleotides of the invention have application in gene therapy for the treatment of diseases that require that a gene be transferred to recipient cells for the purpose of correcting a missing or defective gene, or for the purpose of providing a therapeutic molecule for treatment of a clinical condition. The vectors of the present invention can be adapted to ex vivo and in vitro gene therapy applications.

Thus, the invention provides method for providing therapy for a subject. The recombinant polynucleotide of the invention is administered to a subject in need of gene therapy, such that the administering of the recombinant polynucleotide involves expressing the coding polynucleotide for a therapeutic polypeptide. In one embodiment, the subject is human.

Administration of the polynucleotides. The polynucleotides of the invention can be administered to a subject by any common route (oral, nasal, buccal, rectal, vaginal, or topical), or by subcutaneous, intramuscular, intraperitoneal, or intravenous injection. "Administering" the polynucleotides of the invention may be accomplished by any means known to the skilled artisan. By "subject" is meant any mammal, preferably a human. Polynucleotides of the invention can be administered in the form of a pharmaceutical composition. A "pharmaceutical composition" contains the polynucleotide of the invention in a pharmaceutically acceptable excipient. Examples of pharmaceutically acceptable excipients are provided below.

Polynucleotides of the invention can be administered in vivo or ex vivo. Polynucleotides of the invention can be administered ex vivo by transfer of genetic material to cells, for example hematopoietic stem cells, located outside a subject. Ex vivo transfer, as used herein, utilizes available techniques known to those skilled in the art to remove cells from a subject and introduce into these cells a therapeutic amount of genetic material. Following transfer of the genetic material, the transfected cells can be implanted back in the host subject. In vivo transfer, as used herein, uses available techniques known to those skilled in the art to transfer genetic material into a host cell while the host cell remains part of, or contained in, a multicellular organism.

The pharmaceutical compositions of the invention can be administered topically, intravenously, orally or parenterally or as implants, but even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems (for a brief review of standard methods for drug delivery, see, Langer, 249 Science 1527–1533 (1990)).

A pharmaceutical composition in the form of injectable compositions is typically administered in a pharmaceutically acceptable solvent or diluent and other suitable, physiologic compounds. The composition may contain polynucleotide and about 10 mg of human serum albumin per ml of a phosphate buffer containing NaCl. Other pharmaceutically acceptable excipients include non-aqueous or aqueous solutions and non-toxic compositions including salts, preservatives, buffers and the like. Non-aqueous solutions include propylene glycol, polyethylene glycol, vegetable oil and injectable organic esters such as ethyloleate. Aqueous solutions include water, alcoholic/aqueous solutions, saline solutions, parenteral vehicles such as sodium chloride, Ringer's dextrose, etc. Intravenous vehicles include fluid and nutrient replenishers. Preservatives include antimicrobial, anti-oxidants, chelating agents and inert gases. The pH and exact concentration of the various components the pharmaceutical composition are adjusted according to routine skills in the art. A preferred pharmaceutical composition for topical administration is a dermal cream or transdermal patch.

A pharmaceutical composition can also be administered by injection as an oily suspension. Suitable lipophilic solvents or vehicles include fatty oils, such as sesame oil, or synthetic fatty acid esters, such as ethyl oleate or triglycerides. Moreover, vectors may be combined with a lipophilic carrier such as any one of a number of sterols including cholesterol, cholate and deoxycholic acid. A preferred sterol is cholesterol. Aqueous injection suspensions may contain substances which increase the viscosity of the suspension include, for example, sodium carboxymethyl cellulose, sorbitol, and/or dextran. Optionally, the suspension also contains stabilizers.

Liposome encapsulation provides an alternative formulation for the administration of pharmaceutical compositions of the invention. Liposomes are microscopic vesicles that consist of one or more lipid bilayers surrounding aqueous compartments (see, generally, Bakker-Woudenberg et al., 12 (Suppl. 1) Eur. J. Clin. Microbiol. Infect. Dis. S61 (1993), and Kim, 46 Drugs 618 (1993)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 $\mu$m to greater than 10 $\mu$m. A variety of agents can be encapsulated in liposomes: hydrophobic agents partition in the bilayers and hydrophilic agents partition within the inner aqueous spaces (see, for example, Machy et al., *Liposomes in Pharmacology* (John Libbey 1987), and Ostro et al., 46 American J. Hosp. Pharm. 1576 (1989)). Moreover, it is possible to control the therapeutic availability of the encapsulated agent by varying liposome size, the number of bilayers, lipid composition, as well as the charge and surface characteristics of the liposomes. Recombinant polynucleotides and vectors can be encapsulated within liposomes using standard techniques. A variety of different liposome compositions and methods for synthesis are known to those of skill in the art (see, for example U.S. Pat. Nos. 4,844,904, 5,000,959, 4,863,740, and 4,975,282).

The compounds having the desired pharmacological activity may be administered in a physiologically acceptable carrier to a host for treatment of disease attributable to a defect in gene or protein function. The compounds may also be used to enhance function. The therapeutic agents may be administered in a variety of ways, orally, topically, parenterally e.g. subcutaneously, intraperitoneally, by viral infection, intravascularly, etc., as described above. Inhaled treatments are of particular interest. Depending upon the manner of introduction, the compounds may be formulated in a variety of ways.

The pharmaceutical compositions can be prepared in various forms, such as granules, tablets, pills, suppositories, capsules, suspensions, salves, lotions and the like. Pharmaceutical grade organic or inorganic carriers or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The pharmaceutical compositions are preferably prepared and administered in dose units. Solid dose units are tablets, capsules and suppositories.

Therapeutic methods. The terms "treating," "treatment," and the like mean obtaining a desired pharmacologic or physiologic effect. The effect may be prophylactic in terms of completely or partially preventing a disorder or sign or symptom thereof, or may be therapeutic in terms of a partial or complete cure for a disorder or adverse effect attributable to the disorder. "Treating" covers any treatment of a medical disorder in a subject, and includes:

(a) preventing a disorder from occurring in a subject that may be predisposed to a disorder, but has not yet been diagnosed as having it;

(b) inhibiting a disorder, ie., arresting its development; or (c) relieving or ameliorating the disorder, e.g., cause regression of the disorder.

The term "ameliorate" denotes a lessening of the detrimental affect of the medical disorder in the subject receiving therapy. The term "therapeutically effective" means that the amount used is of sufficient quantity to ameliorate the disorder.

By the term "effective amount" is meant an amount sufficient to obtain the desired effect. An effective amount is generally determined by the physician in each case on the basis of factors normally considered by one skilled in the art to determine appropriate dosages, including the age, sex, and weight of the subject to be treated, the condition being treated, and the severity of the medical condition being treated.

The dosage administered varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 100 mg per kilogram of body weight. The administration of the daily dose can be carried out both by single administration in the form of an individual dose unit or else several smaller dose units and also by multiple administration of subdivided doses at specific intervals. Ordinarily 1.0 to 5, and preferably 1 to 10 mg per kilogram per day given in divided doses 1 to 6 times a day or in sustained release form is effective to obtain desired results. One of one of ordinary skill in the art can use the following teachings describing the methods and techniques for determining clinical dosages to determine the appropriate dosage to use: Spilker, *Guide to Clinical Studies and Developing Protocols* (Raven Press Books, Ltd., New York, 1984) pp. 7–13, 54–60; Spilker, *Guide to Clinical Trials* (Raven Press, Ltd., New York, 1991) pp. 93–101; *Modern Pharmacology*, 2d ed. Craig & Stitzel, eds. (Little, Brown and Co., Boston, 1986) pp. 127–33; *Avery's Drug Treatment: Principles and Practice of Clinical Pharmacology and Therapeutics*, 3d ed., Speight, ed. (Williams and Wilkins, Baltimore, 1987) pp. 50–56; Tallarida et al., *Principles in General Pharmacology* (Springer-Verlag, New York, 1988) pp. 18–20. Typically, dosages used in vitro may provide useful guidance in the amounts useful for in situ administration of the pharmaceutical composition, and animal models may be used to determine effective dosages for treatment of particular disorders. Various considerations are described, e.g., in *Goodman and Gilman's: The Pharmacological Basis of Therapeutics*, 8th ed., Gilman et al. eds. (Pergamon Press, 1990); and *Remington's Pharmaceutical Sciences*, 17th ed. (Mack Publishing Co., Easton, Pa. 1990).

Identifying trans-acting factors that bind to JeT promoter sequences. Also provided are methods of identifying compounds that bind to the JeT promoter. These compounds include trans-acting factors can include, e.g., polypeptides such as transcription factors, which interact preferentially with JeT promoter, or small molecules.

In one embodiment, a compound is identified by performing assays in which a cis-acting KIM-1 nucleic acid sequence is incubated with a test compound. Binding of the compound to the nucleic acid is detected using methods known in the art for assessing nucleic acid binding. For example, binding can be measured using electrophoretic mobility shift assays (EMSA). One way in which an EMSA can be prepared is to incubate together a DNA, which is preferably labeled, containing a KIM-1-derived cis-acting regulatory sequence and the test compound. The mixture is then subjected to electrophoresis, and the migration of the labeled nucleic acid in the presence of the test compound is compared to the migration of the labeled nucleic acid in the absence of the test compound. A difference in mobility indicates that the test compound binds to regulatory sequence.

Any suitable compound can be used as the test compound. In some embodiments, the test compound is obtained from a cellular extract known to contain, or to be suspected of containing, a trans-acting factor. Suitable cells include kidney cells, e.g., COS cells.

Cell-based methods can also be used to identify compounds that modulate activity. For example, a cell containing a JeT promoter operably linked to a nucleic acid encoding a reporter molecule is contacted with a test compound and the reporter molecule mRNA or translated product is measured. mRNA levels and protein levels can be determined using any method known in the art, e.g. using Northern blot hybridization analysis, immunoprecipitations, or immunohistochemistry.

The trans-acting factors can also be identified using in vivo assays. For example, a reporter construct can be constructed in which a reporter gene is under the control of any of the JeT promoter disclosed herein.

The reporter gene can be any gene encoding a protein that can readily be detected. The reporter gene is preferably a gene encoding luciferase. Cells are transfected with the reporter construct that includes a JeT promoter. Transfection can be transient or stable. If desired, the cells are transfected with more than one reporter construct. The transfected cells can then be incubated in the presence or absence of a test compound for an appropriate amount of time and the level of expression of the reporter gene is determined.

Similar assays can also be performed using a cell or nuclear extract instead of cells. Thus, in one embodiment, the invention provides a method for identifying a compound which modulates JeT promoter activity. The method includes incubating a reporter construct that includes any of the regulatory elements according to the invention with a nuclear or cellular extract, or isolated nuclei, in the presence or absence of test compound. Expression of the test compound is then measured, e.g., by including a labeled nucleotide in the reaction and measuring the amount of label incorporated in the product transcribed from the reporter construct. Other methods can also be used to determine the amount of reporter gene expression in this system, such as the measure of the amount of protein encoded by the reporter gene.

In yet another embodiment, compounds that modulate the regulatory elements of the present invention in vivo can be identified in non-human animals. In one embodiment of the invention, a non-human animal, e.g, a mouse, is treated with a compound, such as a compound identified in one of the assays described above. After an appropriate amount of time, the level of activity is determined and compared to its activity in a mouse that has not received the test compound.

Kits. The invention provides kits for use in methods of gene expression. The kit is compartmentalized to receive, in close confinement, one or more containers. One container contains a polynucleotide of the invention. A second container may contain a nucleic acid probe that hybridizes to the other of two strands of polynucleotide of the invention.

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The foregoing description has been presented only for the purposes of illustration and is not intended to limit the invention to the precise form disclosed, but by the claims appended hereto.

We claim:

1. An isolated polynucleotide comprising SEQ. ID. NO:1.

2. The polynucleotide of claim 1, wherein the polynucleotide consists of SEQ. ID. NO:1.

3. An isolated polynucleotide comprising a functional derivative of SEQ ID NO:1 comprising the following elements and spacer sequences connected one to another in linear order:

(a) a first element consisting of SEQ ID NO:6;

(b) a first spacer sequence of any five deoxyribonucleotides;

(c) a second element consisting of SEQ ID NO:6;

(d) a second spacer sequence of any two deoxyribonucleotides;

(e) a third element consisting of SEQ ID NO:4;

(f) a third spacer sequence consisting of any 24 deoxyribonucleotides;

(g) a fourth element consisting of SEQ ID NO:5;

(h) a fourth spacer sequence consisting of any two deoxynucleotides;

(i) a fifth element consisting of SEQ ID NO:6;

(j) a fifth spacer sequence consisting of any five deoxyribonucleotides;

(k) a sixth element consisting of SEQ ID NO:6;

(l) a sixth spacer sequence consisting of any 14 deoxyribonucleotides;

(m) a seventh element consisting of SEQ ID NO:2;

(n) a seventh spacer sequence consisting of any 22 deoxyribonucleotides;

(o) an eighth element consisting of SEQ ID NO:3.

4. An expressable sequence comprising the polynucleotide of claims 1 or 3 operably linked to a coding polynucleotide.

5. The expressable sequence of claim 4, wherein the coding polynucleotide encodes green Fluorescent Protein.

6. A vector comprising the polynucleotide of claims 1 or 3.

7. The vector of claim 6, wherein the vector is pJeTd4E.

8. An isolated eukaryotic cell comprising the polynucleotide of claims 1 or 3.

9. The eukaryotic cell according to claim 8, wherein the cell is a rat hippocampal cell.

* * * * *

SEQUENCE LISTING

<160> NUMBER OF SEQ ID NOS: 8

<210> SEQ ID NO 1
<211> LENGTH: 195
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 1
gaattcgggc ggagttaggg cggagccaat cagcgtgcgc cgttccgaaa gttgcctttt      60
atggctgggc ggagaatggg cggtgaacgc cgatgattat ataaggacgc gccgggtgtg     120
gcacagctag ttccgtcgca gccgggattt gggtcgcggt tcttgtttgt ggatccctgt     180
gatcgtcagt tgaca                                                     195

<210> SEQ ID NO 2
<211> LENGTH: 7
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 2 tatataa                                                                7

<210> SEQ ID NO 3
<211> LENGTH: 7
<212> TYPE: DNA

```
<213> ORGANISM: Artificial Sequence
<220> FEATURE:
<223> OTHER INFORMATION: Description of Artificial Sequence: Chemically
      Synthesized

<400> SEQUENCE: 3 ctagttc                                                                    7

<210> SEQ ID NO 4
<211> LENGTH: 5
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 4 ccaat                                                                      5

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 5
cctttatgg                                                                 10

<210> SEQ ID NO 6
<211> LENGTH: 6
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 6 gggcgg                                                                     6

<210> SEQ ID NO 7
<211> LENGTH: 150
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 7
atcgaattcg ggcggagtta gggcggaggc caatcagcgt gcgccgttcc gaaagttgcc        60
ttttatggct gggcggagaa tgggcggtga acgccgatga ttatataagg acgcgccggg       120
tgtggcacag ctagttccgt cgcagccggg                                        150

<210> SEQ ID NO 8
<211> LENGTH: 56
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 8
cagggatcca caaacaagaa ccgcgaccca atcccggct gcgacggaac tagctg             56
```